United States Patent
Pinney et al.

[11] Patent Number: 5,845,641
[45] Date of Patent: *Dec. 8, 1998

[54] FLUID CONTROL PAD WITH POUCHES

[75] Inventors: Marc E. Pinney, Bedford; Steven R. Robinson, Hurst, both of Tex.

[73] Assignee: Tecnol Medical Products, Inc., Fort Worth, Tex.

[*] Notice: The term of this patent shall not extend beyond the expiration date of Pat. No. 5,713,372.

[21] Appl. No.: 916,995

[22] Filed: Aug. 21, 1997

Related U.S. Application Data

[63] Continuation of Ser. No. 492,640, Jun. 20, 1995, Pat. No. 5,713,372, which is a continuation of Ser. No. 128,632, Sep. 27, 1993, abandoned.

[51] Int. Cl.[6] ............................................. A61B 19/00
[52] U.S. Cl. ............................................. 128/849; 128/851
[58] Field of Search .............................. 128/849–856

[56] References Cited

U.S. PATENT DOCUMENTS

| | | | |
|---|---|---|---|
| Re. 34,512 | 1/1994 | Dowdy et al. | 128/853 |
| 3,646,624 | 3/1972 | Zipf, III | 5/334 |
| 3,785,897 | 1/1974 | Zipf, III | 156/201 |
| 3,809,077 | 5/1974 | Hansen | 128/132 D |
| 3,920,012 | 11/1975 | Patel | 128/134 |
| 4,062,362 | 12/1977 | Schaar | 128/287 |
| 4,169,472 | 10/1979 | Morris | 128/132 D |
| 4,391,010 | 7/1983 | Kronman | 5/484 |
| 4,476,860 | 10/1984 | Collins et al. | 128/132 D |
| 4,627,426 | 12/1986 | Wegener et al. | 128/132 D |
| 4,629,457 | 12/1986 | Ness | 604/382 |
| 4,725,270 | 2/1988 | Schuldt et al. | 604/356 |
| 4,813,944 | 3/1989 | Haney et al. | 604/358 |
| 4,890,628 | 1/1990 | Jackson | 128/849 |
| 4,923,453 | 5/1990 | Bullard, Jr. | 604/356 |
| 5,059,271 | 10/1991 | Taub | 156/306.3 |
| 5,107,859 | 4/1992 | Alcorn et al. | 128/853 |
| 5,143,091 | 9/1992 | Patnode et al. | 128/853 |
| 5,156,167 | 10/1992 | Busch | 128/852 |
| 5,161,544 | 11/1992 | Morris | 128/849 |
| 5,176,667 | 1/1993 | DeBring | 604/356 |
| 5,176,668 | 1/1993 | Bernardin | 604/368 |
| 5,203,350 | 4/1993 | Duncan et al. | 128/840 |
| 5,209,243 | 5/1993 | Glassman | 128/849 |
| 5,221,273 | 6/1993 | Graham | 604/358 |
| 5,222,507 | 6/1993 | Taylor | 128/849 |
| 5,249,320 | 10/1993 | Moretz et al. | 5/484 |
| 5,273,055 | 12/1993 | Ereren | 128/845 |

OTHER PUBLICATIONS

Medical–Surgical Products, 3M Health Care, "Now You can do Your Best Work . . . Drier".
Medical–Surgical Division, 3M Health Care, "Reduce Risks of Exposures to Blood and Body Fluids During Shoulder Procedures, 1067 Steri–Drape™ U–Pouch Shoulder Drape for Fluid Control".
Medical–Surgical Division, 3M Health Care, "Fluid Control Surgical Drapes from 3M . . . help reduce the risk of contact with blood and body fluids".

(List continued on next page.)

*Primary Examiner*—Michael A. Brown
*Attorney, Agent, or Firm*—Dority & Manning, P.A.

[57] ABSTRACT

Apparatus and methods are provided for use in collecting fluids discharged from a patient and liquids used in various types of medical procedures. The apparatus includes a fluid control pad formed from multiple layers of material and one or more pouches attached to the pad. A first layer of film, or backup sheet, is preferably formed from liquid impervious material such as coextruded low density polyethylene and ethyl vinyl acetate polymers. A portion of the backup sheet is covered with a second layer of superabsorbent material and a top layer of cover stock. The first layer of film may be folded to provided pouches disposed longitudinally on opposite sides of the second layer of superabsorbent material. A strip of fiber reinforced porous web type material may be disposed in the opening to each pouch to assist in directing excess fluids from the second layer of superabsorbent material into the associated pouch.

14 Claims, 4 Drawing Sheet

OTHER PUBLICATIONS

3M Health Care, "Surgical Drapes Selection Guide, An expanding line of surgical drapes for improved asepsis and fliud control".

"TRAUMA–SORB™ Absorbent Stretcher Cover" Absorbent Web Engineering, Bowling Green, OH 43202.

Medical–Surgical Division, 3M Health, "Reduce Risks of Exposure to Blood and Body Fluids During Abdominal Surgery, 6658 Ioban 2 Incise Pouch Abdominal Drape for Fluid Control". s

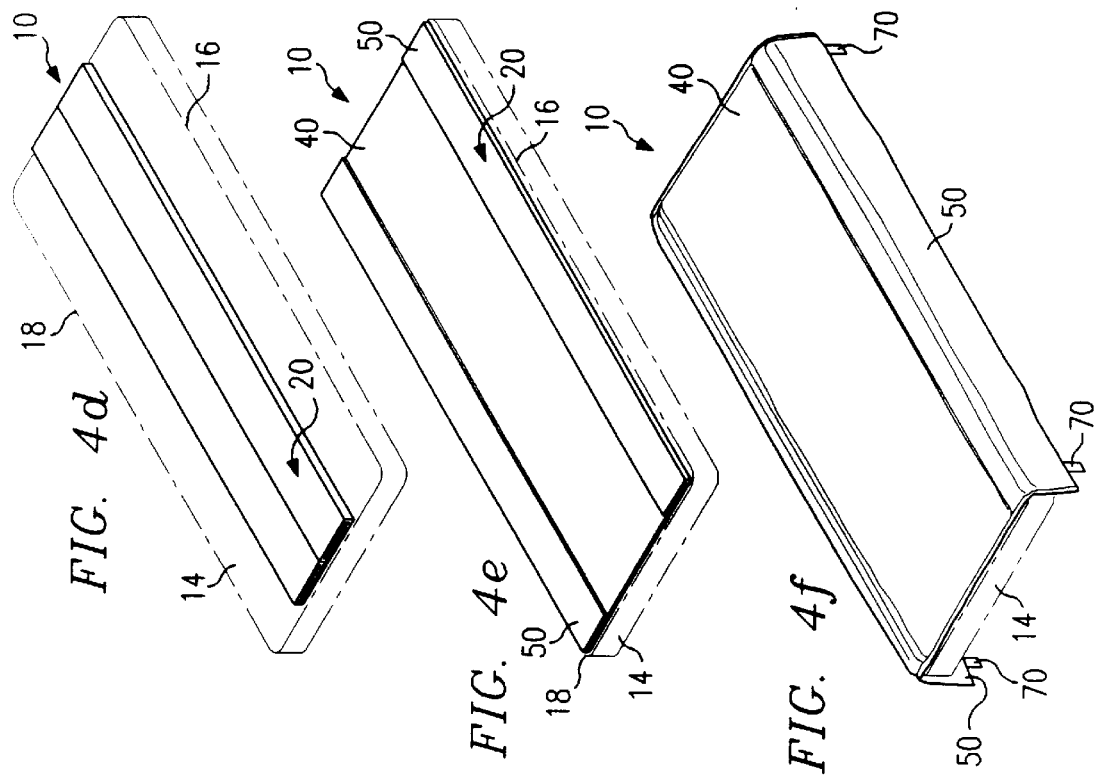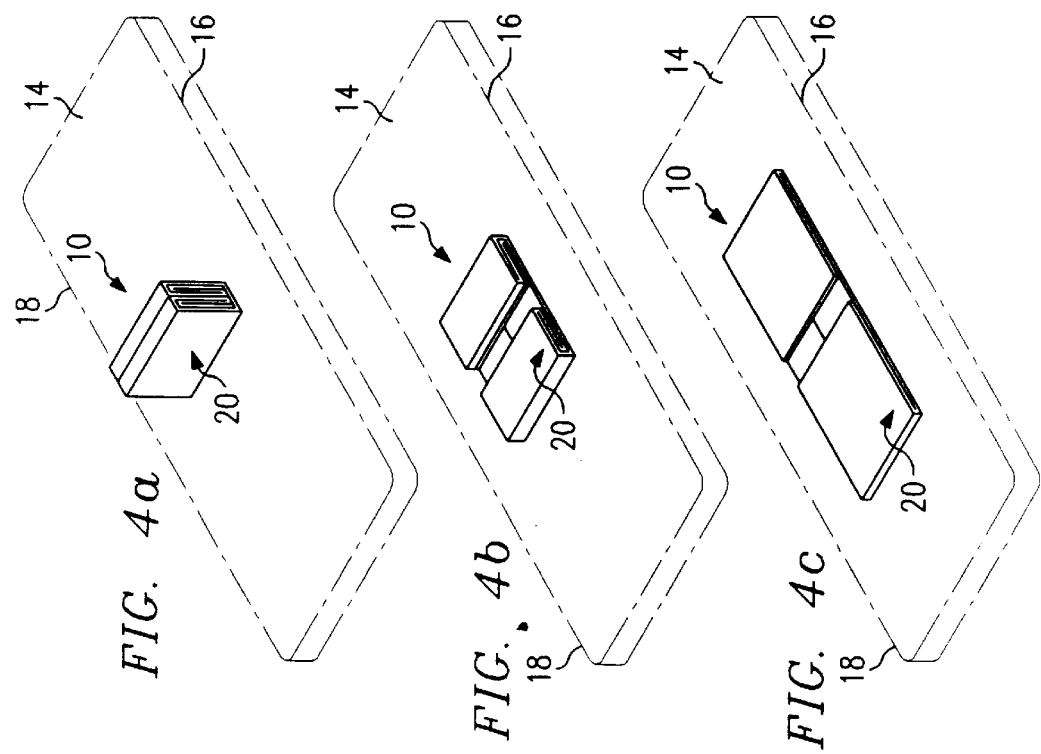

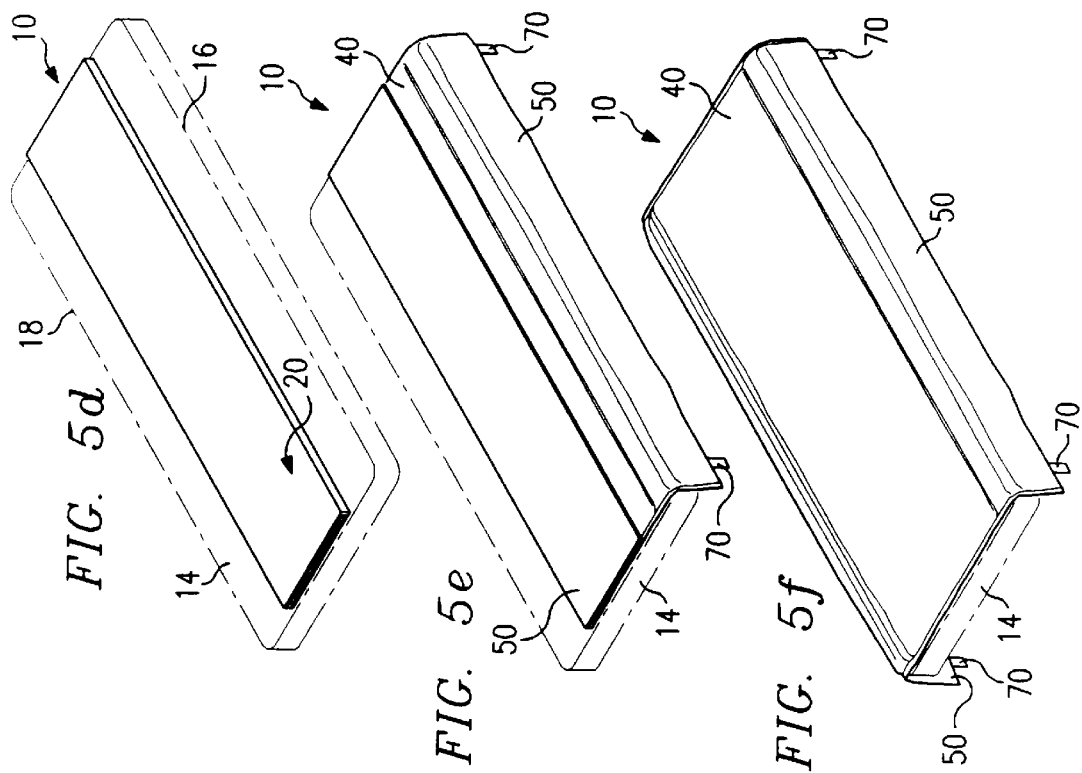
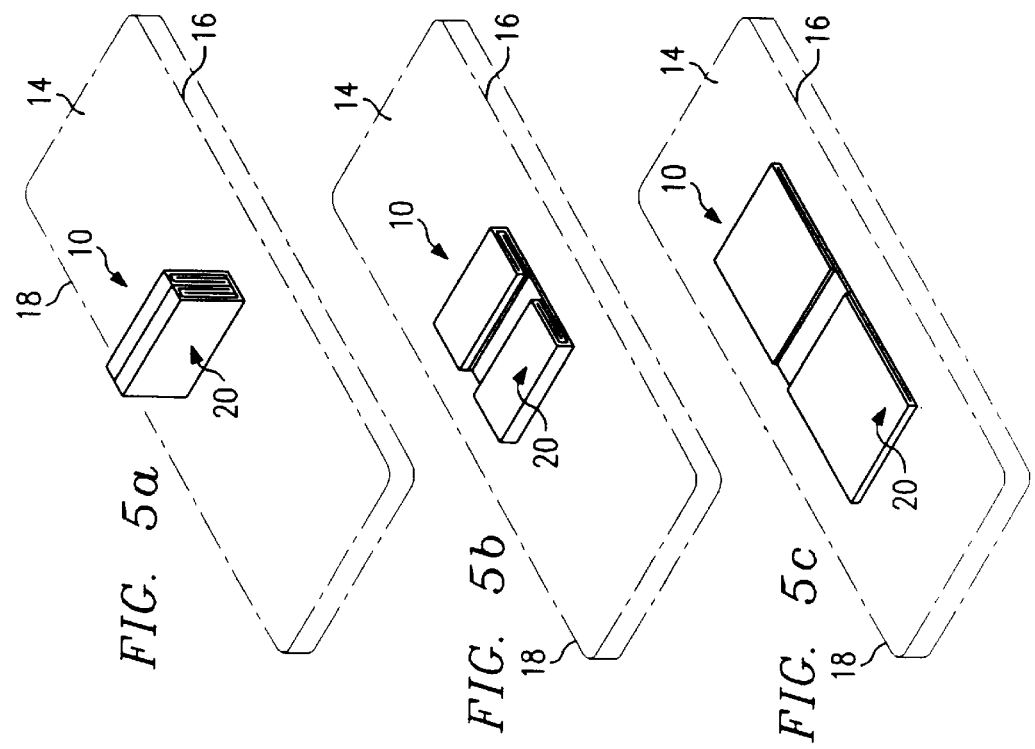

FLUID CONTROL PAD WITH POUCHES

This application is a continuation application of U.S. application Ser. No. 08/492,640 filed Jun. 20, 1995 and entitled "Fluid Control Pad with Pouches," by Marc E. Pinney and Steven R. Robinson, now U.S. Pat. No. 5,713,372, which is a continuation application of U.S. application Ser. No. 08/128,632, filed Sep. 27, 1993 and entitled "Fluid Control Pad with Pouches," abandoned.

TECHNICAL FIELD OF THE INVENTION

The present invention relates to apparatus and methods for controlling fluid. More particularly, and not by way of limitation, this invention relates to a pad for controlling and collecting fluids during emergency trauma situations and other medical or surgical procedures.

BACKGROUND OF THE INVENTION

During many emergency trauma situations and surgical procedures, blood and other body fluids are released. Additionally, many trauma procedures and surgical procedures often require extensive irrigation of the injury or surgical site producing additional potentially contaminated fluids associated with caring for a patient. Many times it is impractical to collect and control such fluids using suction or other equipment.

Blood and other body fluids are potential carriers of various diseases. With the rapid increase in the spread of infectious diseases such as AIDS and Hepatitis B, the use of protective equipment and improved medical procedures to avoid contact with body fluids has become even more important. In a hospital operating room, emergency room, and doctor's office irrigation liquids such as saline solutions are frequently used and become mixed with blood and other body fluids. Therefore, it is often necessary to control relatively large quantities of discharged blood and body fluids mixed with irrigation fluids to minimize any potential for contact between the discharged fluids and medical personnel, operating and emergency room cleanup personnel, and/or laundry room personnel.

When medical procedures such as surgery or emergency trauma treatment are performed, it is common to place the patient on a cloth or sheet. During some medical procedures, pads and towels may be used to absorb discharged liquids. Such liquids may also migrate onto the supporting table or operating room floor as well as possibly contacting medical personnel located in the facility. When the medical procedure is completed, housekeeping personnel must remove the cloth and towels, clean and wipe off the table, and clean and mop the floor. This practice exposes the housekeeping staff and laundry room personnel as well as doctors and nurses to potentially infectious diseases associated with blood and body fluids which have been discharged from the patient. This potentially hazardous situation also occurs during transportation of accident victims to trauma or emergency rooms. Injuries to the head, chest and abdomen often result in the discharge of large quantities of blood and body fluids. Also, such wounds frequently require a substantial amount of irrigation which results in producing an even larger quantity of potentially contaminated liquids.

During surgery, a patient is often covered with a surgical drape designed to expose only the surgical area. Discharged body liquids may flow underneath the drape to possibly a non-sterile area and then wick back up the drape to again come in contact with the sterile surgical field resulting in dangerous contamination. The discharged liquids may also flow along the relatively non-absorbent surface of the drapes onto the floor or the clothing of medical personnel resulting in exposing medical personnel to increased risk of direct contact with these potentially dangerous liquids.

The discharge of bodily fluids may present even more risk of exposure to medical personnel during trauma situations such as transporting patients from the scene of an accident or providing emergency medical services at a trauma center. The control of discharged body fluids and liquids used to treat a patient is frequently much more difficult during trauma situations. Besides the significant health hazards presented by the uncontrolled discharge of such fluids, the floor of an operating room, emergency room or ambulance can quickly become a slippery hazard which may cause personnel to slip and fall.

SUMMARY OF THE INVENTION

In accordance with the present invention, a fluid control pad with pouches and methods for minimizing potential contact with body fluids are provided which substantially eliminate disadvantages and problems associated with previous fluid control equipment and methods used during emergency trauma situations and other medical or surgical procedures. A fluid control pad incorporating the present invention provides enhanced fluid control and containment during medical procedures and allows for safe, quick cleanup and disposal when the medical procedure has been completed.

In accordance with one aspect of the present invention, a fluid control pad is provided including a fluid impermeable backup sheet, an area of superabsorbent material on one side of the backup sheet and a pair of pouches disposed longitudinally on opposite sides of the superabsorbent material. Portions of the backup sheet are preferably folded towards the superabsorbent material to form the pouches. Strips of porous web material may be disposed within the opening for each pouch to allow any excess fluid to flow from the superabsorbent material into the respective pouch. For selected applications, a drain plug may be attached to each pouch to allow controlled removal of any liquids collected within the respective pouch. For other applications, the layer of superabsorbent material may extend into the pouches.

An important technical advantage of the present invention includes providing a relatively large, thin fluid control pad with a layer of superabsorbent material having the capacity to hold three or more liters of liquid. The layer of superabsorbent material in cooperation with the associated pouches provides optimal fluid absorption and collection from any portion of a patient's body. A fluid control pad with pouches incorporating the present invention minimizes potential contact with discharged body fluids and reduces the risk of contamination to doctors, nurses, emergency room personnel, cleanup personnel and laundry room personnel.

A further important technical advantage of a fluid control pad with pouches incorporating the present invention includes improving productivity by reducing the turn around time required to clean up an emergency room, surgical facility, ambulance and other types of vehicle used to transport a trauma patient. The use of the fluid control pad with pouches will extend the service life of emergency room and operating room equipment such as mattresses, trauma tables and gurneys. The fluid control pad with pouches improves safety by reducing the chance of slipping on a wet surface and reduces the risk of exposure by medical, housekeeping, and laundry room personnel to blood and body fluids associated with treating accident victims and trauma patients. The fluid control pad also minimizes potential cross contamination between patients placed on the same trauma table, gurney or other supporting structure.

Still further technical advantages of the fluid control pad and pouches incorporating the present invention include providing at least one layer of cover stock over the layer of superabsorbent material to prevent direct contact between the superabsorbent material and the patient. The cover stock is preferably biocompatible, tear resistant and has a high wicking rate to allow fluids to pass rapidly through the cover stock into contact with the superabsorbent material. The superabsorbent material is selected to have high tensile strength, biocompatibility and to minimize the overall thickness of the fluid control pad, both when packaged and when placed on a stretcher or other patient supporting structure. The superabsorbent material preferably has both a high absorption capacity (three liters or higher) and a high absorption rate. Pouches are provided on one or more edges of the superabsorbent material to collect and contain any fluids discharged from the patient in excess of the absorption capacity of the superabsorbent material. Strips of porous web material are disposed within the opening to each pouch to allow fluids to flow into the respective pouch and to restrict the transfer of liquids from the respective pouch back to the area supporting the patient. The backup sheet is preferably fluid impervious and puncture resistant. The outside of the backup sheet preferably has a high coefficient of friction while the inner surface has a low coefficient of friction. The backup sheet may be formed from coextruded materials having a high degree of flexibility. Tape tabs may be provided on the exterior of the backup sheet proximate the ends of each pouch to secure the fluid control pad to a trauma bed, gurney, mattress or other types of patient supporting structure. The tape tabs preferably include adhesive materials which will adhere to the backup sheet and/or cover stock when wet or dry. The tape tabs may be used to form the fluid control pad around selected portions of the patient's body such as for a head wound. The tape tabs also aid in bundling the fluid control pad for disposal after the medical procedure has been completed.

Still further important technical advantages of the fluid control pad and pouches incorporating the present invention include the use of flame resistant materials which may be disposed of by incineration or sterilization by autoclave or other techniques. Also, the materials forming the fluid control pad and pouches are preferably electrically nonconductive and radiolucent to prevent distortion or clouding of x-ray and other types of patient imaging.

BRIEF DESCRIPTION OF THE DRAWINGS

For a more complete understanding of the present invention and the advantages thereof, reference is now made to the following description taken in conjunction with the accompanying drawings, in which:

FIGS. 4a–4f are schematic representations showing a fluid control pad with pouches incorporating the present invention being unfolded from a first package onto a gurney, stretcher or other type of patient supporting structure; and FIGS. 5a–5f are schematic representations showing a fluid control pad with pouches incorporating the present invention being unfolded from a second package onto a gurney, stretcher or other type of patient supporting structure.

DETAILED DESCRIPTION OF THE INVENTION

Figure 1:
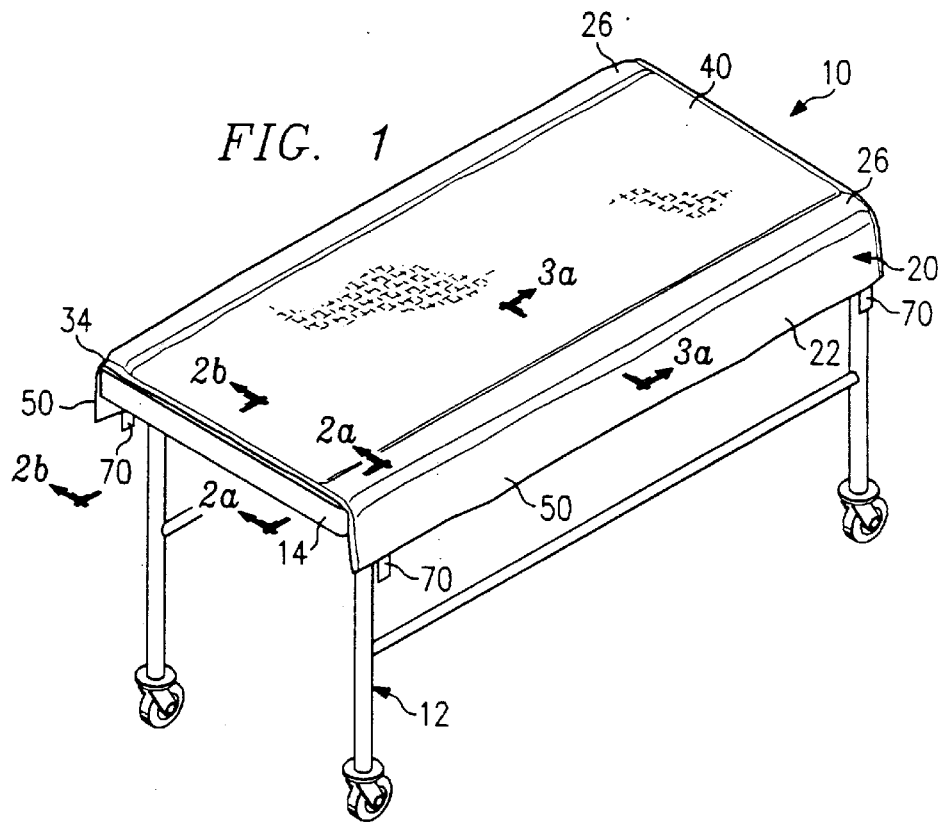
FIG. 1 is an isometric drawing of a hospital gurney covered with a fluid control pad with pouches incorporating the present invention.

The preferred embodiments of the present invention and its advantages are best understood by referring to FIGS. 1–5f of the drawings, like numerals being used for like and corresponding parts of the various drawings.

Fluid control pad 10 is shown in FIGS. 1 through 5f incorporating various components and features of the present invention. The major components of fluid control pad 10 comprise first film layer or backup sheet 20, second layer or superabsorbent material layer 30, and third layer or top layer 40 of cover stock, one or more pouches 50 with an associated strip of porous web type material 60 at the opening to each pouch 50 and a plurality of tape tabs 70. As described later in more detail, fluid control pad 10 and its associated components may be formed from various types of materials and have various geometric shapes.

As shown in FIG. 1, fluid control pad 10 may be placed on supporting structure 14 of gurney 12 used to transport a patient within a hospital or emergency room. Fluid control pad 10 may also be used on a stretcher, operating room table, mattress or any other patient supporting structure 14 associated with providing medical care. Fluid control pad 10 may be used in any area of a hospital including the morgue. For purposes of this application, the terms "medical care" and "medical procedures" include trauma and emergency room procedures, surgical procedures, labor and delivery, emergency medical care, and procedures associated with transportation of trauma patients from the scene of an accident to an appropriate medical facility. Patient supporting structure 14 as shown in FIGS. 3b, 3c, 3d, 4a–4f and 5a–5f may be the top of gurney 12, a mattress, a stretcher, operating room table, trauma table, etc.

Backup sheet or first film layer 20 is preferably formed from material which is resistant to stretching, tearing or punctures and impervious to fluids. Exterior surface 22 of backup sheet 20 preferably has a high coefficient of friction to prevent fluid control pad 10 from sliding relative to the supporting structure 14. Interior surface 24 of backup sheet 20 preferably has a very low coefficient of friction allowing interior surfaces 24a and 24b to slide relatively easy with respect to each other within pouches 50.

Backup sheet 20 is preferably formed from material which is highly flexible to allow easy packaging and storage of fluid control pad 10 and rapid placement of fluid control pad 10 on supporting structure 14. As described later in more detail, FIGS. 4a–4f and 5a–5f show a schematic representations of the flexibility of fluid control pad 10 and the ease with which fluid control pad 10 may be placed on supporting structure 14. For some applications, backup sheet 20 will preferably have an orange color to indicate fluid control and resistance to fluid penetration.

For one embodiment of the present invention backup sheet 20 may be formed from coextruded low density polyethylene and ethyl vinyl acetate polymers. By using coextrusion procedures, ethyl vinyl acetate is used to form exterior surface 22 with a relatively high coefficient of friction and low density polyethylene is used to form interior surface 24 with a relatively low coefficient of friction. The use of coextruded film also produces backup sheet 20 without having any seams.

The typical dimensions for the top of a trauma table used in many emergency rooms and medical facilities include a length of approximately 80–88 inches and a width of approximately 24–29 inches. If fluid control pad 10 is intended for use on such trauma tables, backup sheet 20 will typically comprise a generally rectangular layer of film having an overall length dimension of approximately eighty-one inches and an overall width dimension of approximately fifty-one inches. This width is substantially greater than the width of the intended supporting structure 14 to allow forming pouches 50 from portions of backup sheet 20 extending laterally from second layer 30. The width of backup sheet 20 may be varied depending upon the desired fluid containing capacity of pouches 50 and any other features of the present invention which may be incorporated into a specific fluid control pad. Starting from an initial width of approximately fifty-one inches and second layer 30 having a width of approximately twenty-seven inches, a pair of pouches 50 may be provided with a liquid containing capacity greater than the five liters per pouch 50.

Second layer 30 of absorbent material is preferably disposed on interior surface 24. Second layer 30 will typically have a generally rectangular configuration with dimensions corresponding approximately to the length and width of the intended supporting structure 14. The longitudinal centerline of second layer 30 is preferably aligned with the longitudinal centerline of backup sheet 20. Thus, when fluid control pad 10 is placed on supporting structure 14, the longitudinal edges of second layer 30 will be aligned approximately with the respective longitudinal edges 16 and 18 of patient supporting structure 14. This configuration of backup sheet 20 and second layer 30 results in pouches 50 being disposed adjacent to and approximately parallel with edges 16 and 18 respectively. Second layer 30 will preferably have uniform thickness of absorbent material. Also, second layer 30 will preferably be attached or bonded to interior surface 24 at multiple locations to prevent migration of the absorbent material and maintain uniform thickness.

For most applications, second layer 30 will preferably be formed from superabsorbent material. However, other types of absorbent material may be used for selected medical procedures. Second layer 30 may be formed from materials which both absorb and adsorb fluids depending upon the selected medical procedure.

Various types of superabsorbent material are commercially available for use in forming second layer 30. Examples of such commercially available superabsorbent materials are shown in U.S. Pat. No. 4,629,457 entitled *Absorbent Facing and Method for Making the Same* and U.S. Pat. No. 5,176,668 entitled *Absorbent Structure Designed for Absorbing Body Fluids*. Both of these patents are incorporated by reference for all purposes within this application.

Two of the principle criteria used in selecting the superabsorbent material to form second layer 30 are providing an absorption capacity of at least three liters of liquid and ensuring biocompatibility with a patient placed on fluid control pad 10. Also, the superabsorbent material used to form second layer 30 is preferably disposable by incineration or sterilization using autoclave techniques.

Third layer or top layer 40 is preferably disposed on superabsorbent material layer 30. The longitudinal center line of top layer 40 is preferably aligned with the longitudinal center line of second layer 30 and backup sheet 20. Top layer 40 may be formed from suitable cover stock material which is biocompatible with a patient placed on fluid control pad 10, has good tear resistance and a high wicking rate to allow rapid movement of any fluids discharged from a patient into superabsorbent material layer 30.

If desired, top layer or cover stock layer 40 may be bonded to superabsorbent material layer 30 at selected locations to prevent migration or sliding of the superabsorbent material. For some applications, top layer 40 may be formed from material which would allow fluids to flow from a patient to superabsorbent material layer 30 but will block the return of any fluids from superabsorbent material 30 and/or pouches 50. Examples of such material and their operation may be found in U.S. Pat. No. 3,929,135 issued Dec. 30, 1975 to Thompson and assigned to Proctor and Gamble Company. Such materials are often constructed from a low density polyethylene and include small apertures which prevent liquids from passing therethrough in one direction due to the liquids relatively high surface tension. Other types of non-woven materials or film may be satisfactorily used as desired for top layer 40. For some applications another layer (not shown) of material which allows fluids to flow in only one direction may be placed over layer 30 in addition to cover stock layer 40.

For some applications, it may be desirable to form layer 30 from superabsorbent material which has been sealed or sandwiched between two layers of material such as cover stock 40. The use of the additional cover stock layers (not shown) may be particularly beneficial during selected manufacturing procedures in which layer 30 is bonded or attached with interior surface 24 of backup sheet 20. The present invention allows varying the number of cover stock layers used with the superabsorbent material to optimize the fabrication and performance of fluid control pad 10.

A pair of pouches 50 are preferably formed on each side of fluid control pad 10 extending longitudinally with respect to superabsorbent material layer 30 and cover stock layer 40. As shown in FIGS. 1, 4f and 5f, the width of superabsorbent material layer 30 and cover stock layer 40 is typically selected to allow each pouch 50 to be positioned adjacent to and extend downwardly from the associated longitudinal edge of supporting structure 14. Each pouch 50 also includes longitudinal opening 52 to allow fluid communication with layers 30 and 40. Thus, if the absorption capacity of superabsorbent material layer 30 or a portion of layer 30 is exceeded, any excess fluid discharged from a patient's body and/or used in irrigating the patient will be collected within pouches 50.

Fluid control pad 10 and attached pouches 50 are preferably formed by first selecting the desired type of film material and then cutting backup sheet 20 with length and width dimensions appropriate for the intended supporting structure 14. The desired absorbent material may then be placed on the center portion of backup sheet 20 to form second layer 30 conforming generally with the length and width dimension of the intended supporting structure 14. For many applications, second layer 30 will be formed from superabsorbent material and attached to surface 24 to prevent migration of the superabsorbent material.

Strips 60 of porous web type material are preferably disposed on longitudinal edges 32 and 34 of superabsorbent material layer 30. Various types of reinforced fibers, foam and/or filter media may be satisfactorily used to form strips 60. Strips 60 may also be formed from carded fibers or any thick, lofted material and with the desired flow control characteristics. The location of each strip 60 is selected to correspond approximately with longitudinal edges 16 and 18 of the intended supporting structure 14.

Figure 2A:
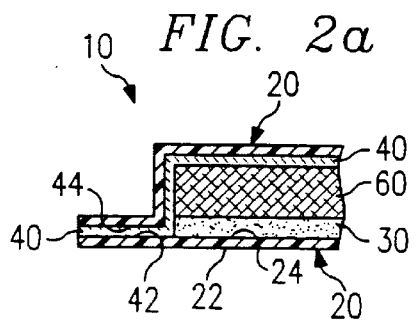
FIG. 2a is a drawing in section with portions broken away, taken along lines 2a—2a of FIG. 1.
Figure 2B:
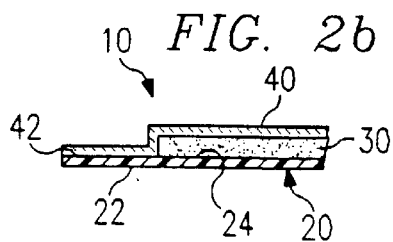
FIG. 2b is a drawing in section with portions broken away, taken along lines 2b—2b of FIG. 1.

Cover stock 40 may next be placed over second layer 30 and bonded to each strip 60 and portions of backup sheet 20 extending from second layer 30 at each end of fluid control pad 10. FIGS. 2a and 2b show bonds 42 and 44 formed between cover stock layer 40 and backup sheet 20 at each end of fluid control pad 10. The portions of backup sheet 20 extending laterally from superabsorbent material layer 30 are then folded over and secured to the respective longitudinal edges of cover stock layer 40 and strips 60. Folding backup sheet 20 in this manner forms the respective pouches 50. As shown in FIGS. 3a through 3d, strips 60 partially define the respective longitudinal openings 52 between the overlapping portions of backup sheet 20 which form the respective pouches 50. Strips 60 cooperated with the associated opening 52 to direct excess fluid to flow into the respective pouch 50. For some applications, pouches 50 may be formed from separate pieces of material and bonded or sealed longitudinally to fluid control pad 10. Separate pouches (not shown) may be attached adjacent to the ends of layers 30 and 40 in addition to the longitudinal edges.

In addition to defining openings 52 into the respective pouches 50, strips 60 may also function as a flow restrictor with respect to fluid flow from the associated pouch 50. Strips 60 are preferably formed from porous web type material which will allow fluid migration into the associated pouch 50, but substantially restrict or limit any rapid or quick fluid flow from the associated pouch 50 back onto the surface of fluid control pad 10 defined by layers 30 and 40. This flow control or flow restricting feature of strips 60 is particularly important both when pouches 50 are substantially filled with fluid and medical personnel are working around supporting structure 14 and when housekeeping personnel are cleaning up the associated medical facility and preparing to dispose of fluid control pad 10 after completion of the medical procedure.

Figure 3A:
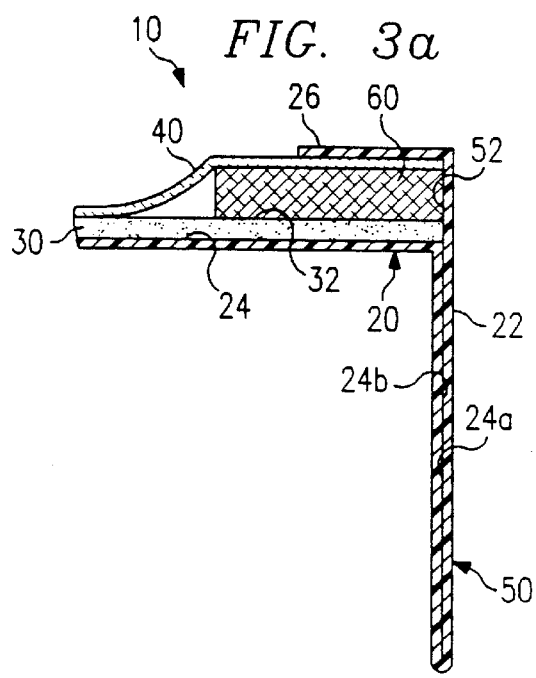
FIG. 3a is a drawing in section with portions broken away, taken along lines 3a—3a of FIG. 1.
Figure 3B:
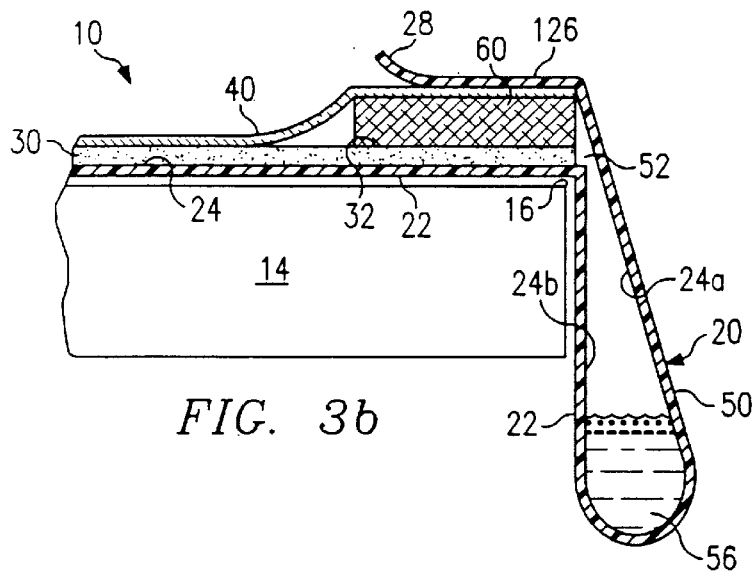
FIG. 3b is a drawing in section with portions broken away showing the fluid control pad of FIG. 1 having a pouch partially filled with liquid.
Figure 3C:
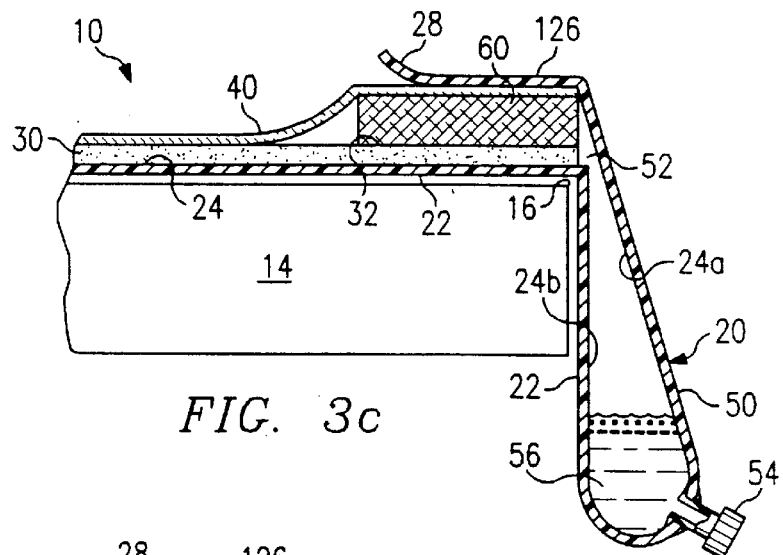
FIG. 3c is a drawing in section with portions broken away showing an alternative embodiment of the present invention wherein a pouch associated with the fluid control pad of FIG. 1 includes a drain plug.
Figure 3D:
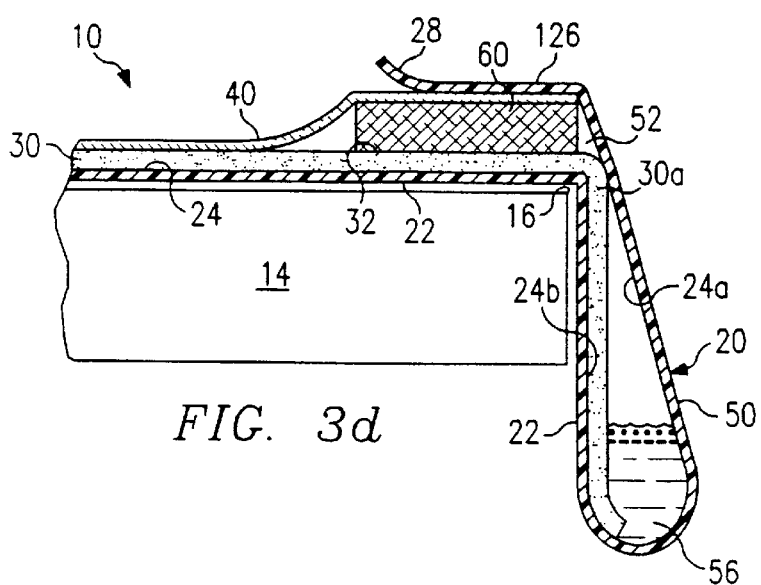
FIG. 3d is a drawing in section with portions broken away showing another alternative embodiment of the present invention wherein superabsorbent material is contained within a pouch associated with the fluid control pad of FIG. 1.

In FIG. 3a portion 26 of backup sheet 20 used to form the associated pouch 50 is fully bonded or sealed with the associated cover stock layer 40 and strip 60. In the embodiment of the present invention shown in FIG. 3b, portion 126 of backup sheet 20 which is used to form the associated pouch 50 is longer than portion 26 shown in FIG. 3a. Flap or lip 28 of portion 126 is not bonded to the adjacent layer 40 and strip 60. The unbonded lip 28 preferably extends longitudinally along second layer 30 and top layer 40. A similar lip 28 (not shown) will preferably be provided on the other strip 60. Lips 28 may be turned up as shown in FIGS. 3b, 3c and 3d to assist with directing excess liquid discharged from a patient or used in irrigating a patient through the associated strip 60 and opening 52 into the respective pouch 50. Lips 28 function as a dam or guide to direct excess fluid flow into the associated pouch 50.

For some applications, flap or lip 28 may be formed from a separate piece of material and disposed longitudinally on each strip 60. For one embodiment of the present invention, a similar lip or flap was formed on portion 26 by reducing the area of the bond between portion 26 and cover stock 40/strip 60. Various methods may be used to provide lip 28 adjacent to each strip 60 to direct or guide fluid flow into the associated pouch 50.

A further alternative embodiment of the present invention is shown in FIG. 3c in which drain plug 54 has been attached to pouch 50. A tube or hose (not shown) may be attached to drain plug 54 to aid in disposal of fluids 56 collected within the associated pouch 50. Various types of drain plug designs may be satisfactorily used with the present invention. Drain plugs 54 may be provided when the associated fluid control pad will be used during medical procedures requiring an unusually large amount of irrigation liquid. Also, drain plug 54 may be provided depending upon the type of disposal equipment and disposal procedures used at the associated medical facility.

Typically pouches 50 extend longitudinally parallel to second layer 30 and edges 16 and 18 of supporting structure 14. Pouches 50 as shown in FIGS. 1, 3a–3d and 4e–4f have a uniform depth from the associated longitudinal edges 16 and 18 to the bottom of each pouch 50. When drain plug 54 is incorporated as part of the associated fluid control pad, the bottom portion of each pouch 50 may be formed with a slope or taper relative to longitudinal edges 16 and 18 to direct fluid flow to drain plug or plugs 54.

For some applications including when drain plugs 54 are not used, it may be desirable to provide pouches 50 which a taper or slope downward from the end of supporting structure 14 on which the patient's head and chest are resting. By providing pouches 50 with this desired taper, fluid will tend to collect at the end of supporting structure 14 away from the area in which a medical procedure is being performed on the patient.

Another alternative embodiment of the present invention is shown in FIG. 3d in which second layer 30 has been partially extended into the associated pouch 50. This extra portion 30a of superabsorbent material will increase the overall absorbing capacity of second layer 30. If desired, pouches (not shown) may also be formed on each end of backup sheet 20 using methods similar to those for forming pouches 50.

As best shown FIGS. 4a through 4f, the present invention allows fluid control pad 10 to be shipped and stored in a relatively small compact package. For some applications, fluid control pad 10 will be stored in a hermetically sealed package with appropriate environmental controls and bacterial controls. The packaging process may include gamma ray sterilization or chemical gas sterilization of fluid control pad 10. The packaging and folding procedures shown in FIGS. 4a–4f are particularly applicable when fluid control pad 10 has been sterilized prior to packaging.

When the package (not shown) has been opened, fluid control pad 10 may be placed on supporting structure 14 as shown in FIG. 4a. Fluid control pad 10 is preferably folded during packaging for quick, easy deployment on supporting structure 14. As shown in FIGS. 4b, 4c and 4d, fluid control pad 10 is first unfolded longitudinally to cover the length of supporting structure 14. Fluid control pad 10 may then be unfolded laterally to complete covering the top of supporting structure 14 as shown in FIG. 4e. Pouches 50 may next be deployed along the longitudinal edges of supporting structure 14 by continuing to laterally unfold fluid control pad 10 as shown in FIGURE 4f.

For many applications, including the present preferred embodiment it may be desirable to modify the folding and packaging of fluid control pad 10 as shown in FIGS. 5a–5f. This alternative folding and packaging is particularly beneficial for those applications in which exterior surface 22 of fluid control pad 10 may have a tendency to adhere or stick to other portions of exterior surface 22. By folding fluid control pad 10 longitudinally in approximately one third portions contact between portions of exterior surface 22 are reduced or eliminated.

As shown in FIGS. 5b, 5c and 5d, fluid control pad 10 is first unfolded longitudinally to cover the length of supporting structure 14 corresponding with the packaging shown in FIGS. 4a–4f. Fluid control pad 10 may then be unfolded laterally to cover edge 16 of supporting structure 14 as shown in FIG. 5e. The associated pouch 50 will be deployed during the unfolding process along longitudinal edge 16. Longitudinal edge 18 may be covered by continuing to laterally unfold fluid control pad 10 as shown in FIG. 5f.

Tape tabs 70 preferably include an adhesive film which will stick to both backup sheet 20 and cover stock 40 when the respective surfaces are both wet and dry. Tape tabs 70 may be provided at the corners of fluid control pad 10. However, tape tabs 70 may also be repositioned depending upon the function being performed by tape tabs 70. These functions include securing fluid control pad 10 to the associated patient supporting structure 14, securing pouches 50 to minimize the possibility of fluid spills, conforming fluid control pad 10 with a patient such as forming a hood around a patient's head and bundling fluid control pad 10 to aid in disposal when the associated medical procedure has been completed.

In addition to tape tabs 70, other mechanisms may be used to position fluid control pad 10 on supporting structure 14. Examples of these mechanisms include placing one or more adhesive strips (not shown) on the portion of exterior surface 22 which contacts supporting structure 14. Also, wire stays or flexible strips of wire or plastic (not shown) may be disposed in various portions of backup sheet 20 to assist in securing fluid control pad 10 to supporting structure 14. Examples of such molding strips are shown in U.S. Pat. No. 5,150,703 to Vance M. Hubbard, et al. U.S. Pat. No. 5,150,703 is incorporated by reference for all purposes in this application. Also, one or more straps (not shown) may be secured to exterior surface 22 of fluid control pad 10 for use in securing fluid control pad 10 to supporting structure 14. These straps may be attached to exterior surface 22 using Velcro strips, hooks and/or other attaching mechanisms.

Various types of sealing and/or bonding techniques may be used to attach backup sheet 20 with superabsorbent material layer 30, strips 60 and cover stock layer 40 as shown in FIGS. 1–3d. Examples of these bonding techniques include ultrasonic sealing, adhesives, thermal-impulse and/or thermal sealing. The bonding techniques and the selection of materials used to manufacture fluid control pad 10 are preferably selected to produce a product which is flame resistant, biocompatible, disposable by incineration or autoclave, electrically non-conductive and radiolucent with respect to x-ray or other medical imaging techniques.

Although the present invention and its advantages have been described in detail, it should be understood that various changes, substitutions, and alterations can be made herein without departing from the spirit and scope of the invention as defined in the following claims.

What is claimed is:

1. A fluid control pad for placement under a patient's body to absorb and control body fluids discharged during a medical procedure comprising:

the fluid control pad having a generally rectangular configuration with a length and a width;

a backup sheet of liquid impermeable material for placement on a supporting structure;

the backup sheet having a generally rectangular configuration defined in part by four edges with length approximately equal to the length of the fluid control pad and a width greater than the width of the fluid control pad;

a layer of absorbent material disposed intermediate the four edges of the backup sheet;

a layer of cover stock disposed on the layer of absorbent material for placement of the patient's body on the layer of cover stock;

at least one portion of the backup sheet folded over and secured to one edge of the absorbent material layer and to a portion of the cover stock layer disposed on the absorbent material layer to partially define a pouch which extends adjacent to and communicating with the layer of absorbent material; and the pouch providing means for collecting body fluids therein.

2. The fluid control pad as defined in claim 1 further comprising:

a plurality of tape tabs on the exterior of the backup sheet; and each tape tab including an adhesive film.

3. The fluid control pad as defined in claim 1 wherein the backup sheet further comprises an exterior surface having a first coefficient of friction and an interior surface having a second coefficient of friction with the first coefficient of friction higher than the second coefficient of friction.

4. The fluid control pad as defined in claim 1 wherein the pouch further comprises a drain plug and a taper formed in a bottom portion of the pouch for removing any fluids contained within the pouch.

5. The fluid control pad as defined in claim 1 further comprising:

a longitudinal opening formed by the pouch adjacent to the layer of absorbent material to allow fluid flow into the pouch; and means for allowing excess fluid to flow from the layer of absorbent material into the pouch through the associated longitudinal opening and for restricting fluid flow from the pouch back to the layer of absorbent material.

6. The fluid control pad as defined in claim 1 further comprising a plurality of tape tabs on the exterior of the backup sheet and each tape tab including an adhesive film for releasably securing the fluid control pad to the supporting structure and for bundling the fluid control pad for disposal following completion of the medical procedure.

7. A fluid control pad for placement on a supporting structure under a patient's body to absorb and control body fluids discharged during a medical procedure comprising:

a backup sheet of liquid impermeable material having an exterior surface for placement on the supporting structure;

the backup sheet having a generally rectangular configuration defined in part by a pair of opposite longitudinal edges and a pair of opposite lateral edges;

a layer of absorbent material disposed on an interior surface of the backup sheet intermediate the edges of the backup sheet;

the absorbent material layer having a generally rectangular configuration with a pair of opposite longitudinal edges and a pair of opposite lateral edges smaller than the respective lateral edge of the backup sheet;

a layer of cover stock disposed on the layer of absorbent material for placement of the patient's body on the layer of cover stock;

a pair of pouches with one of the pouches extending respectively along one longitudinal edge of the layer of absorbent material and the other pouch extending respectively along the opposite longitudinal edge of the layer of absorbent material;

a respective longitudinal opening formed as part of each pouch adjacent to the layer of absorbent material and communicating with each pouch; and a strip of porous web material disposed on the absorbent material adjacent to the opening of each pouch.

8. A method of forming a fluid control pad for placement on a patient supporting structure between a patient's body and the supporting structure during a medical procedure, the patient supporting structure having a generally rectangular configuration with a length, width and four edges, comprising the steps of:

forming a film layer from fluid impervious material with an exterior surface for placement on the patient supporting structure;

placing a generally rectangular layer of superabsorbent material within the proximate center of the film layer and the layer of superabsorbent material extending longitudinally and laterally over a middle portion of the film layer;

placing a layer of cover stock over the superabsorbent material layer for placement of the patient's body thereon;

folding at least one edge of the film layer over a selected portion of the superabsorbent material layer to form a pouch attached to the fluid control pad and extending from the superabsorbent material layer for collecting liquids therein; and selecting the size of the film layer and the superabsorbent material layer to allow the pouch to extend along at least a portion of the length of the patient supporting structure and to extend downwardly from one edge of the patient supporting structure when the fluid control pad is disposed thereon.

9. The method of forming a fluid control pad as defined in claim 8 further comprising the steps of:

placing a strip of porous web material on the selected portion of the superabsorbent material layer; and folding the at least one edge of the film layer over the porous web material to form the pouch with the porous web material further defining in part an opening into the pouch.

10. The method of forming a fluid control pad as defined in claim 8 further comprising the steps of:

forming the layer of film with a generally rectangular configuration;

forming the layer of superabsorbent material with a length and a width corresponding approximately with the respective length and width of the patient supporting structure and with portions of the film layer extending laterally and longitudinally from the layer of superabsorbent material; and folding opposite edges of the film layer over respective portions of the superabsorbent material layer to form first and second pouches along respective longitudinal edges of the superabsorbent material layer with each pouch having an opening to allow collecting the liquids therein.

11. The method of forming a fluid control pad as defined in claim 10 further comprising the steps of:

placing a strip of porous web material on each of the selected portions of the superabsorbent material layer; and folding the opposite edges of the film layer over the respective strip of porous web material to partially define a longitudinal opening from the superabsorbent material layer to the respective first and second pouch.

12. The method of forming a fluid control pad as defined in claim 11 further comprising the steps of:

placing the layer of cover stock over the superabsorbent material layer and the strips of porous web material; and folding each longitudinal edge of the film layer over a portion of the cover stock layer and the respective porous web material to form the respective pouch on each side of the fluid control pad.

13. The method of forming a fluid control pad as defined in claim 8 further comprising the steps of:

placing a strip of porous web material on the selected portion of the superabsorbent material layer;

placing the layer of cover stock on the superabsorbent material layer and the strip of porous web material; and folding the at least one edge of the film layer over the strip of porous web material to partially define the pouch with the strip of porous web material disposed within an opening to the pouch.

14. The method of forming a fluid control pad as defined in claim 8 further comprising the step of placing a plurality of tape tabs with each tape tab including an adhesive film on the exterior of the film layer.

\* \* \* \* \*